United States Patent
Ye et al.

(10) Patent No.: US 10,424,395 B2
(45) Date of Patent: Sep. 24, 2019

(54) COMPUTATION PIPELINE OF SINGLE-PASS MULTIPLE VARIANT CALLS

(71) Applicant: Sentieon Inc., Mountain View, CA (US)

(72) Inventors: Jun Ye, Palo Alto, CA (US); Wei Zhou, Saratoga, CA (US); Luoqi Chen, Saratoga, CA (US); Hanying Feng, San Jose, CA (US); Hong Chen, San Jose, CA (US); Xiaofeng Liu, Campbell, CA (US)

(*) Notice: Subject to any disclaimer, the term of this patent is extended or adjusted under 35 U.S.C. 154(b) by 643 days.

(21) Appl. No.: 15/080,532

(22) Filed: Mar. 24, 2016

(65) Prior Publication Data

US 2016/0283654 A1 Sep. 29, 2016

Related U.S. Application Data

(60) Provisional application No. 62/139,148, filed on Mar. 27, 2015.

(51) Int. Cl.
*G16B 30/00* (2019.01)
*G16B 20/00* (2019.01)

(52) U.S. Cl.
CPC ............. *G16B 30/00* (2019.02); *G16B 20/00* (2019.02)

(58) Field of Classification Search
None
See application file for complete search history.

(56) References Cited

PUBLICATIONS

Pabinger et al. A survey of tools for variant analysis of next-generation genome sequencing data Briefings in Bioinformatics vol. 15, pp. 256-278 (Year: 2013).*

* cited by examiner

*Primary Examiner* — John S Brusca
(74) *Attorney, Agent, or Firm* — Jun He Law Offices P.C.; James J. Zhu (57) ABSTRACT

The present disclosure provides a computer-implemented method of analyzing variants from a plurality of nucleic acid sequence reads. The method uses a computation pipeline having at least one invariable module and at least one variable module, wherein the variable module depends on a variable parameter. The method includes executing on a processor the steps of receiving the plurality of nucleic acid sequence reads; setting a plurality of values for the variable parameter; passing the plurality of the nucleic acid sequence reads through the invariable module to generate an intermediate output; passing the intermediate output through the variable module for multiple rounds, each round using one of the variable values; and generating a plurality of variant calls.

20 Claims, 3 Drawing Sheets

COMPUTATION PIPELINE OF SINGLE-PASS MULTIPLE VARIANT CALLS

CROSS-REFERENCE TO RELATED APPLICATIONS

This application claims priority to U.S. provisional patent application No. 62/139,148, filed Mar. 27, 2015, the disclosure of which is incorporated herein by reference.

FIELD OF THE INVENTION

The present invention generally relates to genomic sequencing data analysis.

BACKGROUND OF THE INVENTION

Next-generation sequencing (NGS) technology has provided a powerful tool to produce a gigantic amount of biological data that will shed light on path towards personalized medicine. While the cost of high throughput genome sequencing is decreasing in terms of merely acquiring sequence data, the analysis and interpretation of these large-scale sequencing data remains to pose a major challenge. To call variants from NGS data, many aligners and variant callers have been developed and composed into diverse pipelines. A typical pipeline contains an aligner and a variant caller: the former maps the sequencing reads to a reference genome, and the latter identifies variant sites and assigns a genotype to the subjects. In going through the pipeline, users often need to set many parameters in order to properly analyze the sequencing data. Importantly, some parameters need to be optimized for accurately calling the variant, e.g., on the basis of the type of cells or the ethnic groups from which the sample is prepared. However, due to the enormous computation required for each run of the pipeline, going through the entire variant call pipeline to test each parameter setting is practically infeasible. Therefore, there is continuing need to develop new methods and systems to optimize parameter settings for analyzing NGS data.

SUMMARY OF THE INVENTION

In one aspect, the present disclosure provides a computer-implemented method for analyzing variants from a plurality of nucleic acid sequence reads using a computation pipeline, which comprises an invariable module and a variable module, wherein said variable module depends on a variable parameter. In certain embodiments, the method comprises executing on a processor the steps of: receiving the plurality of said nucleic acid sequence reads; setting a plurality of variable values for the variable parameter; passing the plurality of said nucleic acid sequence reads through said invariable module to generate an intermediate output; passing said intermediate output through said variable module for multiple rounds, each round using one of said variable values; and generating a plurality of variant calls.

In certain embodiments, said variable module is a variant call module.

In certain embodiments, said variable parameter is a prior probability. In some examples, said prior probability is a genome-wide SNP probability, an insertion and deletion (Indel) probability, a Phred-scaled gap extension sequencing error probability or a Phred-scaled gap open sequencing error probability.

In certain embodiments, said invariable module is a mapping module, a duplicate marking module, a local realignment module, a base quality recalibration module or a combination thereof.

In certain embodiments, said invariable module depends on an invariable parameter, and wherein the method further comprises the step of setting an invariable value for the invariable parameter.

In certain embodiments, said invariable parameter is selected from the group consisting of: an alignment seed for the mapping module, a seed length for the mapping module, an allowed maximum number of mismatches for mapping module, a scoring strategy for choosing the non-duplicate among candidates for duplicate marking module, a maximum offset between two duplicate clusters for duplicate marking module, a penalty for mismatch in the local realignment module, a gap opening in the local realignment module, a gap extension in the local realignment module, pair-HMI in the variant call module, a recalibration table in the base quality recalibration module, a variant call mode in the variant call module and a threshold for variant call in the variant call module.

In certain embodiments, the method described supra further comprises the step of: reviewing at least one of said variant calls; setting an adjusted value for the variable parameter; passing said intermediate output through said variable module using the adjusted value; and generating an updated variant call.

In another aspect, the present disclosure provides a computer-implemented method for analyzing variants from a plurality of nucleic acid reads using a computation pipeline, which comprises an invariable module and a variable module, wherein said variable module depends on a variable parameter. The method comprises executing on a processor the steps of: receiving a plurality of nucleic acid sequence reads; setting a plurality of variable values for the variable parameter; passing the plurality of said nucleic acid sequence reads through said variable module for multiple rounds to generate a plurality of intermediate outputs, each round using one of the plurality of said variable values; passing each of said intermediate outputs through said invariable module; and generating a plurality of variant calls.

In yet another aspect, the present disclosure provides a computer-implemented method for analyzing variants from a plurality of nucleic acid reads using a computation pipeline, which comprises an invariable module and a variable module, wherein said variable module depends on a variable parameter. The method comprises executing on a processor the steps of: receiving a plurality of nucleic acid sequence reads; setting a first variable value for the variable parameter; passing the plurality of said nucleic acid reads through said invariable module to generate an intermediate output; passing the intermediate output for a first round using the first variable value; generating a first variant call; reviewing the first variant call; setting a second variable value for the variable parameter; passing the intermediate output through said variable module for a second round using the second variable value; and generating a second variant call.

In another aspect, the present disclosure provides a non-transitory computer-readable medium with instructions for analyzing variants from a plurality of nucleic acid sequence reads using a computation pipeline described herein. In certain embodiments, the computation pipeline comprises an invariable module and a variable module, wherein said variable module depends on a variable parameter.

In certain embodiments, the instructions when executed by a processor, performs the steps comprising: receiving the plurality of nucleic acid sequence reads; setting a plurality of variable values for the variable parameter; passing the plurality of said nucleic acid sequence reads through said invariable module to generate an intermediate output; passing the intermediate output through said variable module for multiple rounds, each round using one of said variable values; and generating a plurality of variant calls.

In certain embodiments, the instructions when executed by a processor, performs the steps comprising: receiving a plurality of nucleic acid sequence reads; setting a first value for the variable parameter; passing the plurality of said nucleic acid reads through said invariable module to generate an intermediate output; passing the intermediate output through said variable module for a first round using the first variable value; generating a first variant call; reviewing the first variant call; setting a second variant value for the variable parameter; passing the intermediate output through said variable module for a second round using the second variable value; and generating a second variant call.

These and other features, aspects, and advantages of the present invention will become better understood with regard to the following description, appended claims and accompanying drawings.

DETAILED DESCRIPTION OF THE INVENTION

In the Summary of the Invention above and in the Detailed Description of the Invention, and the claims below, and in the accompanying drawings, reference is made to particular features (including method steps) of the invention. It is to be understood that the disclosure of the invention in this specification includes all possible combinations of such particular features. For example, where a particular feature is disclosed in the context of a particular aspect or embodiment of the invention, or particular claim, that feature can also be used, to the extent possible, in combination with and/or in the context of other particular aspects and embodiments of the invention, and in the invention generally.

It is understood that as used herein and in the appended claims, the singular forms "a," "an," and "the" include the plural reference unless the context clearly dictates otherwise. Thus, for example, a reference to a "variable module" is a reference to one or more variable modules, and includes equivalents thereof known to those skilled in the art and so forth.

Where reference is made herein to a method comprising two or more defined steps, the defined steps can be carried out in any order or simultaneously (except where the context excludes that possibility), and the method can include one or more other steps which are carried out before any of the defined steps, between two of the defined steps, or after all the defined steps (except where the context excludes that possibility).

Where a range of value is provided, it is understood that each intervening value, to the tenth of the unit of the lower limit unless the context clearly dictate otherwise, between the upper and lower limit of that range and any other stated or intervening value in that stated range, is encompassed within the disclosure, subject to any specifically excluded limit in the stated range. Where the stated range includes one or both of the limits, ranges excluding either or both of those included limits are also included in the disclosure.

It will be appreciated that for simplicity and clarity of illustration, where appropriate, reference numerals have been repeated among the different figures to indicate corresponding or analogous elements. In addition, numerous specific details are set forth in order to provide a thorough understanding of the embodiments described herein. However, the embodiments described herein can be practiced without these specific details. In other instances, methods, procedures and components have not been described in detail so as not to obscure the related relevant function being described. Also, the description is not to be considered as limiting the scope of the implementations described herein. It will be understood that descriptions and characterizations of the embodiments set forth in this disclosure are not to be considered as mutually exclusive, unless otherwise noted.

Definitions

The following definitions are used in the disclosure:

The term "comprises" and grammatical equivalents thereof are used herein to mean that other components, ingredients, steps, etc. are optionally present. For example, an article "comprising" (or "which comprises") components A, B, and C can consist of (i.e., contain only) components A, B, and C, or can contain not only components A, B, and C but also one or more other components.

The term "at least" followed by a number is used herein to denote the start of a range beginning with that number (which may be a range having an upper limit or no upper limit, depending on the variable being defined). For example, "at least 1" means 1 or more than 1. The term "at most" followed by a number is used herein to denote the end of a range ending with that number (which may be a range having 1 or 0 as its lower limit, or a range having no lower limit, depending upon the variable being defined). For example, "at most 4" means 4 or less than 4, and "at most 40%" means 40% or less than 40%. In this disclosure, when a range is given as "(a first number) to (a second number)" or "(a first number)-(a second number)," this means a range whose lower limit is the first number and whose upper limit is the second number. For example, 25 to 100 mm means a range whose lower limit is 25 mm, and whose upper limit is 100 mm.

As used herein, the term "nucleic acid sequence read" refers to a nucleic acid sequence determined by a sequencing method. The nucleic acid sequence can be DNA or RNA sequence. In certain embodiments, the nucleic acid reads are genomic DNA sequencing data. In certain embodiments, the nucleic acid reads are exome sequencing data. Classical DNA sequencing method includes chain termination method (Sanger sequencing). In certain embodiments, "nucleic acid read" refers to a nucleic acid sequence determined by next-generation sequencing (high—throughput sequencing) methods, which parallelize the sequencing process, producing thousands or millions of sequence concurrently. Next-generation sequencing methods include, for example, sequencing by synthesis technology (Illumina), pyrosequencing (454), ion semiconductor technology (Ion Torrent sequencing), single-molecule real-time sequencing (Pacific Biosciences) and sequencing by ligation (SOLiD sequencing). Depending on the sequencing methods, the length of each nucleic acid read may vary from about 30 bp to more than 10,000 bp. For example, Illumina sequencing method using SOLiD sequencer generates nucleic acid reads of about 50 bp. For another example, Ion Torrent Sequencing generates nucleic acid reads of up to 400 bp and 454 pyrosequencing generates nucleic acid reads of about 700 bp. For yet another example, single-molecule real-time sequencing methods may generate nucleic acid read of 10,000 bp to 15, 000 bp. Therefore, in certain embodiments, the nucleic acid sequence reads have a length of 30-100 bp, 50-200 bp, or 50-400 bp.

The term "variant" when used in the context of nucleic acid sequence refers to a nucleic acid sequence that is different from a reference. Typical nucleic acid sequence variant includes without limitation single nucleotide polymorphism (SNP), short deletion and insertion polymorphisms (Indel), copy number variation (CNV), microsatellite markers or short tandem repeats and structural variation.

As used herein, the term "computer-implemented method" means that the method is carried out in a computer, e.g., a computer program executed by a CPU. A computer, as used herein, refers to a device (for general or specific purposes) that can be programmed to perform a set of arithmetic or logical operations automatically. Computers, as used herein, include without limitation personal computers, workstations, servers, mainframes and supercomputers. The computer can be a stand-alone system, networked system or a virtual machine residing in a computing cloud. The methods described herein can be implemented with multithreading or other parallel computing methods.

As used herein, a "computation pipeline" or a "pipeline" refers to a set of data processing elements connected in series, wherein the output of one element is the input of the next element. In certain embodiments, the output of one operation is automatically fed to the next, following operation. As used herein, the elements of a computational pipeline may be called "modules." In certain embodiments, a pipeline is linear and one-directional. In certain embodiments, a primarily one-directional pipeline may have some communication in the other direction. In certain embodiments, a pipeline may be fully bi-directional.

As used herein, a "module" refers to a data processing element within a computation pipeline. A set of modules connects in series to form a computation pipeline. Usually, a module receives an input data, performs certain function based on the input data, and generates an output data, which is then used as an input data for the next following module. In certain embodiments, a module can be further divided into several sub-modules, e.g., connected in series.

The related term "invariable module" refers a module having no variable parameters, i.e., when passing a data set through a computation pipeline, only one set of value is set to the parameter(s) of the module. However, it shall be noted that when passing different data sets through the computational pipeline, different sets of value may be set to the parameter(s) of the module.

The term "variable module" refers a module having at least one variable parameter. It is understood that in addition to depending on a variable parameter, a variable module may also depend on one or more invariable parameter.

The term "parameter," as used herein, refers to a reference, feature or value that users need to set in a computation pipeline or module. When passing a data set through the computation pipeline or module, the reference, feature, or value is passed to a function, procedure, subroutine, command, or program. Related term "invariable parameter" means a parameter, when a computation pipeline or module is run, that is set as one value. In contrast, "variable parameter" refers to a parameter to which more than one value is set when running a computation pipeline or module.

The term "value" used herein refers to a number or feature set to a parameter. Accordingly, when a computation pipeline is used to analyze nucleic acid sequence data, the number or feature is passed to a function, procedure, command or program of the computation pipeline described in the present disclosure. The exact number or feature that can be set to a parameter can be understood in the context of the module and the parameter discussed infra. For example, the value for a parameter of prior probability that is used in the variant call module can be 0.0005, 0.0008, 0.001 or 0.002. For another example, the value for a parameter of penalty of mismatch that is used in the alignment module can be +1 to +5. The term "variable value" used herein refers to value set for a variable module. Typically, when a single-pass multiple variant call computation pipeline is used, multiple values are set to a variable parameter. Accordingly, the value for the variable parameter in the computation pipeline can be varied. In contrast, the term "invariable value" used herein refers to value set for an invariable module. Typically, when a single-pass multiple variant call computation pipeline is used, a single value is set for the invariable module. Consequently, the value for the invariable parameter in the computation pipeline is fixed.

The term "passing" when used in the context of passing a data set (e.g., nucleic acid sequence reads), through a pipeline or a module" means analyzing the data set using the pipeline or module. Typically, in passing the pipeline or module, the data set is fed to the pipeline or module as in input. The pipeline or module then use the data set to run the function, procedure, command or program contained within and generate an output (e.g., a second data set). In certain embodiments, the output can be used as an input to be fed to a second pipeline or module. In certain embodiments, passing a data set through a module also includes using the data set as indirect input for the module. For example, in a computation pipeline comprising at least two modules connected in series, the data set is passed as input to the first module, which generates an output that is passed as input of the second module. In such situation, the data set is regarded as being passed through the second module even though it is not used as direct input of the second module. The related term "round" when used to describe passing a data set through a module refers to the number of time the function, procedure, subroutine, command, or program of the module is run.

The term "non-transitory computer-readable medium" refers to any computer-readable media with the sole exception being a transitory, propagating signal. Non-transitory computer-readable medium includes, without limitation, a volatile memory, a nonvolatile memory, a soft disk, a hard disk, a memory stick, a register memory, a processor cache and a RAM.

The term "mapping" or "mapping to a reference," as used herein, means aligning nucleic acid sequence reads to a reference, e.g., a reference genome, whose sequence is already known. Various programs and algorithms have been developed to map nucleic acid sequence reads to a reference (see, Flicek P, Birney E. (2009) Sense from sequence reads: methods for alignment and assembly, Nat Methods 6(11 Suppl): S6-S12; Neilsen R, Paul J S et al. (2011) Genotype and SNP calling from next-generation sequencing data. Nat Rev Genet 12: 443-52; Ruffalo M et al. (2011) Comparative analysis of algorithms for next-generation sequencing read alignment. Bioinformatics 27: 2790-96; Patnaik S et al. (2012) Customisation of the exome data analysis pipeline using a combinatorial approach. PLoS ONE 7: e30080). Among the various programs and algorithms, Burrows-Wheeler Aligner (BWA), which is based on Burrows-Wheeler transformation, (Li H, Durbin R (2009) Fast and accurate short rad alignment with Burrows-Wheeler transform. Bioinformatics 25: 1754-60) demonstrates a good balance between running time, memory usage and accuracy, and commonly used in different computation pipelines.

Computation Pipeline for Analyzing Nucleic Acid Sequence Reads

Rapid advances in next-generation sequencing technologies have transformed biological and biomedical research over the past several years. Depending on the sequencing method and system used, the number of nucleic acid reads generated is often more than several million. For example, MiniSeq from Illumina generates up to 25 million reads per run, and the HiSeq series from Illumina generates up to 5 billion reads per run. With the gigantic amount of sequencing data generated, there is an imminent need for powerful computational tools to analyze and interpret these large-scale sequencing data.

Many computation pipeline composed of various aligners and variant callers have been developed, including, without limitation, SAMtools (Li H et al. (2009) The sequence alignment/Map format and SAMtools. Bioinformatics 25: 2078-79), glftools (Abecasis lab (2010) Abecasis lab GLF tools), GATK (DePristo M A et al. (2011) A framework for variation discovery and genotyping using next-generation DNA sequencing data. Nat Genet 43: 491-98; McKenna A et al. (2010) The genome analysis Toolkit: a MapReduce framework for analyzing next-generation DNA sequencing data. Genome Res 20: 1297-1303) and Atlas (Challis D et al. (2012) An integrative variant analysis suite for whole exome next-generation sequencing data. BMC Bioinformatics 13: 8).

Figure 1:
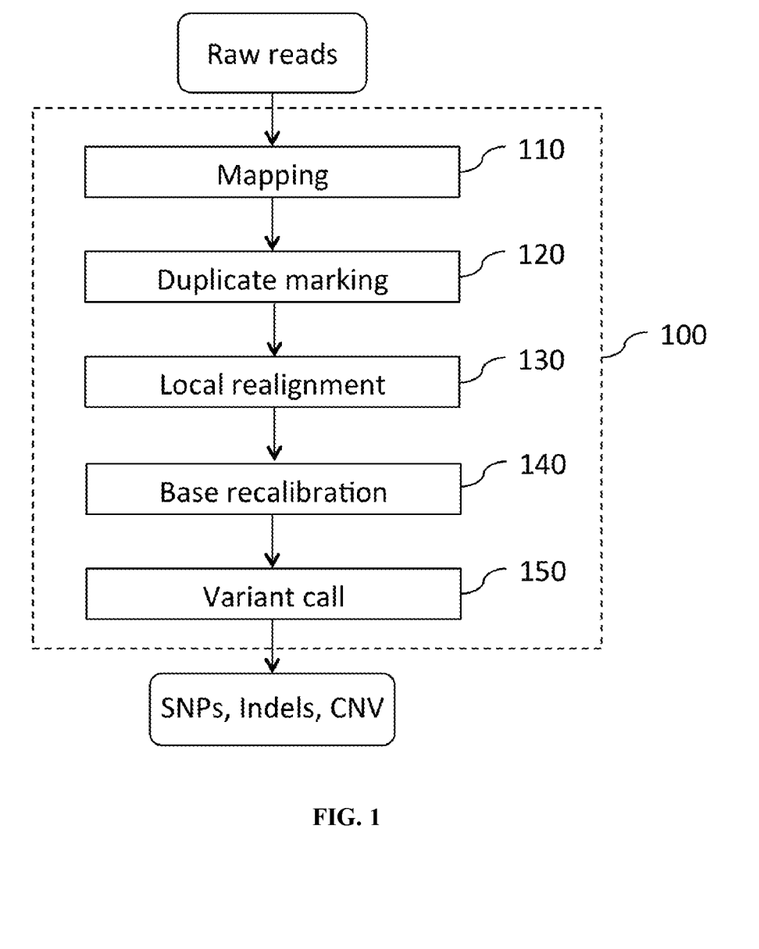
FIG. 1 shows an exemplary computation pipeline.

An exemplary computation pipeline for analyzing nucleic acid sequence reads is illustrated in FIG. 1. As shown in FIG. 1, a computation pipeline 100 for analyzing nucleic acid sequence reads comprises an array of modules connected in series.

Initially, raw read data are fed to the mapping module 110 to align the short sequencing reads to a reference. The mapping module 110 aligns the nucleic acid sequence reads to a reference, e.g., a reference genome, whose sequence is already known. Various programs and algorithms have been developed to map nucleic acid sequence reads to a reference (see, Flicek P, Birney E. (2009) Sense from sequence reads: methods for alignment and assembly, Nat Methods 6(11 Suppl): S6-S12; Neilsen R, Paul J S et al. (2011) Genotype and SNP calling from next-generation sequencing data. Nat Rev Genet 12: 443-52; Ruffalo M et al. (2011) Comparative analysis of algorithms for next-generation sequencing read alignment. Bioinformatics 27: 2790-96; Patnaik S et al. (2012) Customisation of the exome data analysis pipeline using a combinatorial approach. PLoS ONE 7: e30080). Among the various programs and algorithms, Burrows-Wheeler Aligner (BWA), which is based on Burrows-Wheeler transformation, (Li H, Durbin R (2009) Fast and accurate short rad alignment with Burrows-Wheeler transform. Bioinformatics 25: 1754-60) demonstrates a good balance between running time, memory usage and accuracy, and are commonly used in different computation pipelines.

The output (e.g., a SAM (Sequence Alignment/Map) file or a BAM (binary version of SAM) file) of the mapping module is then fed to the duplicate marking module 120 to remove PCR duplicate. During the preparation of DNA samples for sequencing, PCR is often used to amplify the fragments, thus generating duplicates. Ideally prepared samples often generate several percent (e.g., about 4%) reads that are identical copies of each other, i.e., duplicates. Sometime, 30% to 70% of the reads are duplicates. Algorithms for marking/removing duplicates have been described by Wysoker A et al (PicardTools) and Li H et al (Li H et al. (2009) The sequence alignment/Map format and SAMtools. Bioinformatics 25: 2078-79).

The reads with duplicates marked/removed is fed to a local realignment module 130 to improve on the alignments of the reads. Typically, realignment occurs in areas around insertions and deletions (Indel) in the reads relative to the reference and is to map the read with one end on one side of the Indel and the rest on the other side. When the reads are originally mapped to the reference, no information is available about the existence of an Indel. Thus, reads that are mapped to such regions, but that only have a short part of the read representing the region on one side of the Indel, will typically not be mapped properly across the Indel, but instead be mapped with this end unaligned, or into the Indel region with many mismatches. The local alignment module 130 uses information from the other reads mapping to a region containing an Indel, including reads that are located more centered across the Indel and thus have been mapped with ends on either side of the Indel. As a result, an alternative mapping, as good as or better than the original, can be generated.

Algorithms for local realignment have been described by Homer et al. (Homer N (2010) Improved variant discovery through local re-alignment of short-read next generation sequencing data using srma. Genome Biol 11(10): R99). In the first step, alignment information of all input reads are collected in an efficient graph-based data structure, which is essentially similar to a de-Bruijn graph. This realignment graph represents how reads are aligned to the reference sequence and how reads overlap each other. In the second step, metadata are derived from the graph structure that indicate at which alignment positions realignment could potentially improve the read mapping, and also provides hypotheses as to how reads should be realigned to yield the most concise multiple alignment. In the third step the realignment graph and its metadata are used to actually perform the local realignment of each individual read.

DePristo et al. described an alternative algorithm for local realignment (DePristo M A et al. (2011) A framework for variation discovery and genotyping using next-generation DNA sequencing data. Nat Genet 43: 491-98). The algorithm begins by first identifying regions for realignment where (i) at last one read contains an Indel, (ii) there exists a cluster of mismatching bases or (iii) an already known Indel segregates at the site (e.g., from dbSNP (single nucleotide polymorphism database), which is a public archive for genetic variation within and across different species developed and hosted by the National Center for Biotechnology Information (NCBI), which contains a range of molecular variation including (1) SNPs; (2) short deletion and insertion polymorphisms, (3) microsatellite markers or short tandem repeats (STRs), (4) multinucleotide polymorphisms (MNPs), (5) heterozygous sequences, and (6) named variants). At each region, haplotypes are constructed from the reference sequence by incorporating any known Indels at the site, Indels in reads spanning the site or from Smith-Waterman alignment of all reads that do not perfectly match the reference sequence (Durbin et al. (1998) Biological Sequence Analysis: Probabilistic Models of Proteins and Nucleic Acids. (Cambridge University Press, Cambridge, UK)). For each haplotype Hi, reads are aligned without gaps to Hi and scored according to:

$$L(R_j | H_i) = \prod_k L(R_{j,k} | H_{i,k})$$

$$L(R_{j,k} | H_{i,k}) = \begin{cases} 1 - \varepsilon_{j,k} \approx 1 & R_{j,k} = H_{i,k} \\ \varepsilon_{j,k} & R_{j,k} \neq H_{i,k} \end{cases}$$

$$L(H_i) = \prod_j L(R_j | H_i)$$

wherein Rj is the jth read, k is the offset in the gapless alignment of Rj and Hi and $\varepsilon_{jk}$ is the error rate corresponding to the declared quality score for the kth base of read Rj, The haplotype Hi that maximizes L(Hi) is selected as the best alternative haplotype. Next, all reads are realigned against just the best haplotype Hi and the reference ($H_0$), and each read Rj is assigned to Hi or $H_0$ depending on whichever maximizes $L(R_j|H)$. The reads are realigned if the log odds ratio of the two-haplotype model is better than the single reference haplotype by at least five log units:

$$\frac{L(H_0, H_i)}{L(H_0)} = \frac{\prod_j \max[L(R_j | H_i), L(R_j | H_0)]}{\prod_j L(R_j | H_0)}$$

This discretization reflects a tradeoff between accuracy and efficient calculation of the full statistical quantities. In certain example, the algorithm operates on all reads across all individuals simultaneously, which ensures consistency in the inferred haplotypes among all individuals, a critical property for reliable Indel calling and contrastive analyses such as somatic SNP and Indel calling. Typically, the realigned reads are written to a SAM/BAM file for further analysis.

The output of the local realignment module is then fed to the base recalibration module 140, which provides empirically accurate base quality scores for each base in every read. In certain examples, the base recalibration module 140 also corrects for error covariates like machine cycle and dinucleotide context, as well as supporting platform-specific error covariates like color-space mismatches for SOLiD and flow-cycles for 454. Exemplary algorithm for base recalibration module 140 has been described by DePristo M A et al. (DePristo M A et al. (2011) A framework for variation discovery and genotyping using next-generation DNA sequencing data. Nat Genet 43: 491-98). Typically, for each lane, the algorithm first tabulates empirical mismatches to the reference at all loci not known to vary in the population (dbSNP build 129), categorizing the bases by their reported quality score (R), their machine cycle in the read (C) and their dinucleotide context (D). The empirical quality score for each category can be estimated as the following:

$$\text{mismatch}(R, C, D) = \sum_{r \in R} \sum_{c \in C} \sum_{d \in D} \sum_{br,c,d} b r, c, d \neq bref$$

$$\text{bases}(R, C, D) = \sum_{r \in R} \sum_{c \in C} \sum_{d \in D} |\{b, r, c, d\}|$$

$$Q_{empirical}(R, C, D) = (\text{mismatch}(R, C, D) + 1)/(\text{bases}(R, C, D) + 1)$$

The covariates are then broken into linearly separable error estimates and the recalibrated quality score $Q_{recal}$ is calculated as:

$$recal(r, c, d) = Q_r + \Delta Q(r) + \Delta\Delta Q(r, c) + \Delta\Delta Q(r, d)$$

$$\Delta Q = Q_{empirical}(R, C, D) - \left(\sum_\rho \varepsilon_r \times N_r\right) / \text{bases}(R, C, D)$$

$$\Delta Q(r) = Q_{empirical}(r, C, D) - Q_r - \Delta Q$$

$$\Delta Q(r, c) = Q_{empirical}(r, c, D) - (\Delta Q_r + \Delta Q(r))$$

$$\Delta Q(r, d) = Q_{empirical}(r, C, d) - (\Delta Q_r + \Delta Q(r))$$

where each $\Delta Q$ and $\Delta\Delta Q$ are the residual differences between empirical mismatch rates and that implied by the reported quality score for all observations conditioning only on $Q_r$ or on both the covariate and $Q_r$; wherein $Q_r$ is the base's reported quality score and $\varepsilon_r$ is its expected error rate; $b_{r,c,d}$ is a base with specific covariate values, and r, c, d and R, C, D are the sets of all values of reported quality scores, machine cycles and dinucleotide contexts, respectively.

The output from the base recalibration module 140 is then fed to variant call module 150 to discover all sites with statistical evidence for an alternate allele present among the reads including SNPs, short indels and copy number variations. Typically, a variant call module uses an algorithm or statistical model that is usually specified by mathematical equations that relate one or more random variables and possibly other non-random variables. For example, based on the read depths and variant counts, a probability value indicating the confidence level that a specific variant at a specific location is a true positive is calculated using a statistical model based method and a localized method using a reference sample.

Various algorithms have been developed for variant calling. For example, Mapping and Assembly with Quality (MAQ) (Li H et al. (2008) Mapping short DNA sequencing reads and calling variants using mapping quality scores. Genome Res 18: 1851-58) and SOAPsnp (Li R et al. (2009) SNP detection for massively parallel whole-genome resequencing. Genome Res 19: 1124-32) use fixed prior probability value for heterozygote and nucleotide—read error. SeqEM (Martin E R et al. (2010) SeqEM: an adaptive genotype-calling approach for next generation sequencing studies. Bioinformatics 26: 2803-10) introduces multiple-sample genotype calling via an adaptive approach employing the expectation-maximization (EM) algorithm to estimate the model parameters. SAMtools uses a revised MAQ model to estimate sequencing error. The glftools family (glfSingle, glfMultiples, and polymutt) call SNPs from pre-generated genotype likelihood files (GLF). GATK adopts the MapReduce philosophy to parallel programming for simple Bayesian modeling (Dean J, Ghemawat S (2008) MapReduce: simplified data processing on large clusters. Commu ACM 51: 107-13). Atlas2 employs logistic regression models trained on validated whole-exome capture sequencing data rather than regular likelihood calculation s and has been shown to have high sensitivity (Ji H P (2012) Improving bioinformatics pipelines for exmome variant calling. Genome Med 4: 7).

In certain embodiments, the sequence of the modules in the computation pipeline described above can be shuffled. For example, the duplicate marking module can be placed downstream of the local realignment module.

In certain embodiments, a computation pipeline may have fewer modules as described above. For example, Liu X et al described a pipeline that skips local realignment module, duplicate marking module and base recalibration module (Liu X et al. (2013) Variant callers for next-generation sequencing data: a comparison study. PLoS ONE 8(9): e75619).

Computation Pipeline of Single-pass Multiple Setting

In passing the reads through a computation pipeline, the users need to set values to many parameters. For example, in a variant call module, the user needs to specify certain prior probabilities. "Prior probability" refers to the probability distribution representing prior knowledge about the distribution of variants, which is incorporated to facilitate variant calling. In a variant call module adopting GATK algorithm, for example, the user needs to specify the genome-wide SNP probability and the Indel probability. The "genome-wide SNP probability" means the probability of a variation in a single nucleotide that may occur at some specific position in the genome, where each variation is present to some appreciable degree within a population. The "Indel probability" refers to the probability of the occurrence of an insertion or the deletion of bases in the DNA of an organism. Similarly, in a variant call module using SAMTools algorithm, the user needs to specify Phread-scaled gap extension sequencing error probability and Phred-scaled gap open sequencing error probability.

There are many other parameters that users need to set in the pipeline. For example, in a local alignment module, the user needs to specify the penalties for mismatch (a scoring system used for aligning a small portion of fragmented genetic sequence, e.g., in order to make more accurate decisions in aligning reads, mutations are annotated as gaps in the sequence, and gaps are penalized via various penalty scoring methods, which allows for the optimization of sequence alignment in order to obtain the best alignment possible based on the information available), gap opening (the cost required to open a gap of any length) and gap extension (the cost required to extend the length of an existing gap). In base quality recalibration, the user needs to specify the recalibration table (a table built up to track the number of matches/mismatches for each set of covariates and to assign a well-calibrated probability to each variant call in a call set) or the parameters to compute the recalibration table, and quantization level in the base quality output. The user may also need to specify variant call mode (the value that appears most often in a set of data representing an estimate of variant frequency and some measure of confidence) and thresholds for variant calling (the minimum confidence threshold at which the program should emit variant sites as called; if a site's associated genotype has a confidence score lower than the calling threshold, the program will emit the site as filtered; this threshold separates high confidence calls from low confidence calls), pair-HMM (pair-hidden Markov Model, a variant of the basic HMM that is especially useful for finding sequence alignments and evaluating the significance of the aligned symbols) and the transition probability used therein, etc.

To better evaluate the variants, users need to change the parameters or explore the variants under a range of parameters settings. As an example, the user might want to see how the probability of the identified variant changes when the SNP/Indel's prior probabilities are changed, so to explore various situations of the sample. For example, a higher prior probability may need to be used if the sample is from cancer cells. Different prior probabilities may also be used based on the sample's ethnic group, since certain ethnic groups may have higher variant probability than others. If the user does not know ahead of time the optimal prior probabilities, they may want to explore the variants properties over a range of prior probabilities, so to cover all possible situations.

One approach to do such parameter exploration is to go through the entire computation pipeline again for each parameter setting. For example, after a user runs through the pipeline with the most probable parameter setting and has reviewed the called variants, the user may decide to go back and change the parameters and re-run the whole variant call pipeline, to look at what would change for those called variants. Such an iterative re-run of the whole pipeline could be very time-consuming or prohibitively expensive, resulting in few parameter settings being explored, hence may result in some biologically significant information being missed.

Therefore, in one aspect, the present disclosure provides methods and systems of analyzing variants from a plurality of nucleic acid sequence reads using a computation pipeline that comprises at least one invariable module and at least one variable module, wherein the at least one variable module depends on a variable parameter. In certain embodiments, the method comprises executing on a processor the steps of: receiving the plurality of nucleic acid sequence reads; setting a plurality of values for the variable parameter; passing the plurality of nucleic acid sequence reads through the at least one invariable module for a single time; passing the plurality of nucleic acid sequence reads through the at least one variable module for multiple times, wherein each time the at least one variable module uses one of the plurality of values for the variable parameter; and generating a plurality of variant calls.

Figure 2:
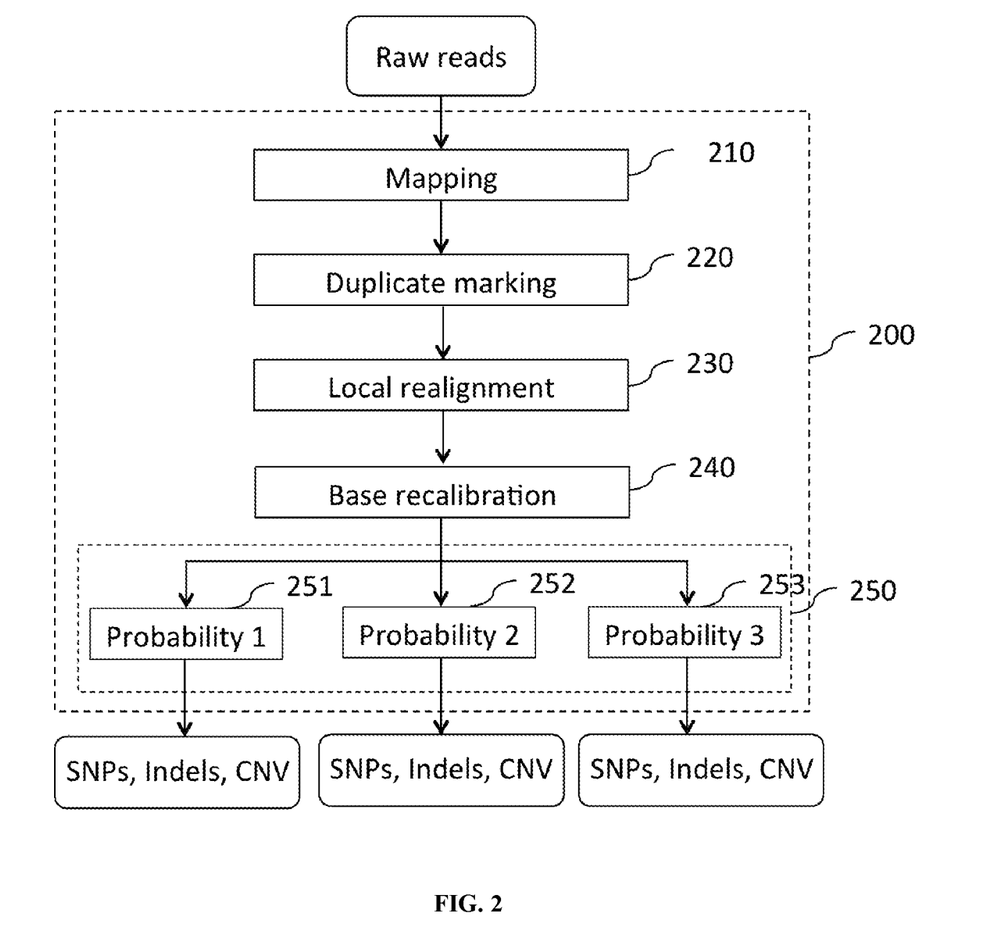
FIG. 2 shows an exemplary computation pipeline comprising at least one invariable module and at least one variable module.

An exemplary computation pipeline comprising at least one invariable module and at least one variable module is illustrated in FIG. 2. As shown in FIG. 2, a computation pipeline 200 for analyzing nucleic acid sequence reads comprises an array of modules connected in series.

Raw read data are fed to the mapping module 210 to align the short sequencing reads to a reference. Parameters of the mapping module 210, such as alignment seed, the seed length and the allowed maximum number of mismatches are set with one value for each parameter. The output of the mapping module 210 is fed to the duplicate marking module 220. The parameters of the duplicate marking module 220, such as the scoring strategy for choosing the non-duplicate among candidates, the maximum offset between two duplicate clusters in order to consider them optical duplicates are set with one value for each parameter. The output of the duplicate marking module 220 is fed to the local realignment module 230. Parameters of the local realignment module 230, including the penalties for mismatch, gap opening and gap extension are set with one value for each parameter. The output of the local realignment module 230 is fed to base recalibration module 240. Parameters for the base recalibration module 240, including values for the recalibration table (described supra in detail) are set with one value for each parameter. The output of the base recalibration module 240 is fed to the variant call module 250. Multiple sets of values 251, 252, 253 are set for the parameters, e.g., prior probabilities. As a result, the input data is passed through the variant call module 250 multiple times by using each set of the values (251, 252 and 253) for the parameters. In one example, a 3×3 matrix: SNP (0.002, 0.001, 0.0005)×Indel (0.0002, 0.0001, 0.00005) is explored, wherein SNP 0.002 means the SNP prior probability is set as 0.002, and so on. Consequently, the variant call module is run 9 times under the 3×3 different parameter combinations, producing 9 variant call output.

In certain embodiments, some of the computations in the variant call module 250, such as read filtering, which only depends on read base qualities and alignment, and certain conditional probability of bases, do not depend on the prior probability, so can be run only once.

By removing redundant computations, multiple outputs from the variant call module 250 using multiple parameter settings can be obtained from a single pass of the computation pipeline 200. The total computation performed in such a single pass is only a small fraction of the computation otherwise required by the multiple full-pipeline re-runs.

After such a single-pass multiple-parameter-setting run, the outputs from the variant call module 250 can be visually displayed as a function of the parameter set, enabling users to have a better visual understanding of the variants.

Computation Pipeline of Incremental Exploration

Instead of computing and outputting results of multiple parameter settings in a single pass, the pipeline can compute and output results under a single parameter setting in first pass. The outputs from each module during the first pass, i.e., intermediate results are saved. A user can adjust the parameter setting for at least one module of the pipeline based on the results, e.g., variant call from the first pass and passes the reads through the pipeline for a second time. In the second pass, the pipeline can automatically identify the intermediate results that do not need to re-computed, and use them directly in the new parameter setting. As such, the computation for additional parameter settings only compute those portions of the pipeline that are affected by the difference between the new and previous parameter settings, hence saving computations in parameter exploration. The method is preferred also because it may eliminate exploration of some unnecessary parameter settings.

Therefore, in another aspect, the present disclosure provides methods and systems of analyzing variants from a plurality of nucleic acid reads using a computation pipeline that comprises at least one invariable module and at least one variable module, wherein the at least one variable module depends on a variable parameter. In certain embodiments, the method comprises executing on a processor the steps of: receiving a plurality of nucleic acid sequence reads; setting a first variable value for the variable parameter; passing the plurality of nucleic acid reads through the at least one invariable module for a single time; passing the at least one variable module for a first time using the first variable value; generating a first variant call; setting a second variable value for the variable parameter based on the first variant call; passing the plurality of nucleic acid reads through the at least one variable module for a second time using the second variable value set for the variable parameter; and generating a second variant call without passing the at least one invariable module.

Figure 3:
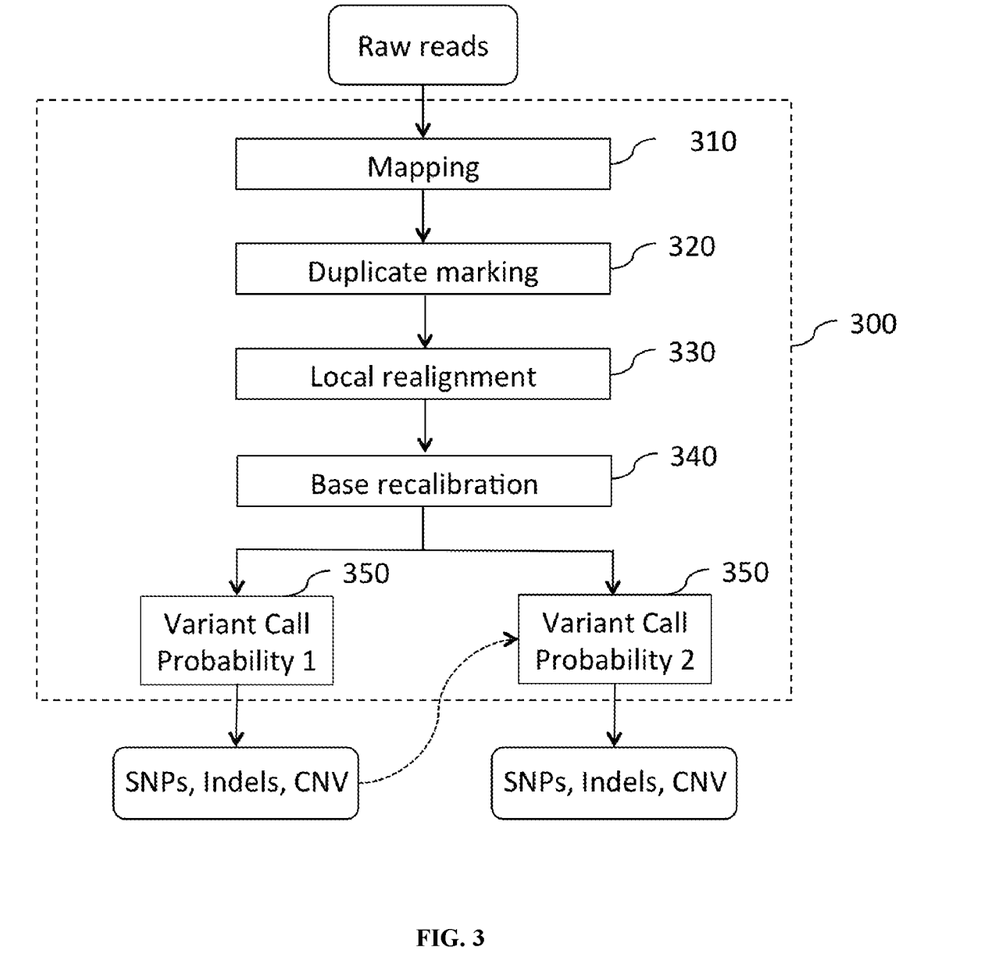
FIG. 3 shows an exemplary computation pipeline comprising at least one invariable module and at least one variable module.

FIG. 3 illustrates an exemplary computation pipeline 300 of incremental exploration for analyzing nucleic acid sequence reads. The computation pipeline 300 comprises an array of modules connected in series. When raw read data are fed to the computation pipeline 300, it passes through the mapping module 310, the duplicate marking module 320, the local realignment module 330, the base recalibration module 340 and the variant call module 350 as described supra. A first value set is used for the prior probabilities in the variant call module 350, and a first variant call result is obtained. On the basis of the first variant call result, a second set of values are set for the probabilities in the variant call module 350. The output from the base recalibration 340 is then fed to the variant call module 350 to generate a second variant call result.

In certain embodiments, the "single-pass-multiple-setting" mode and the "incremental exploration" mode can be combined. For example, the pipeline runs through parameter settings in first single pass, producing a plurality of variant calls, and also save intermediate outputs. After reviewing the multiple variant calls produced in the first single pass, the user may adjust the parameters in one or more modules. Then the pipeline can pick up the intermediate results from the first pass, reusing in the new pass, thus saving computation in new pass.

Alignment Module

In another aspect, the present disclosure provides methods and systems to improve alignment-to-reference computation. During alignment, some parameters are also selected by users, for example, the alignment seed, the seed length, the allowed maximum number of mismatches, etc. When users explore the alignment parameters, the reads that have perfect match with the reference do not need to be re-run through the alignment in each setting, but can be done once and used for all cases. Only unmapped reads and the reads that have mismatches with the reference need to go through multiple alignments under the different parameter settings.

Assembly Pipeline

In yet another aspect, the present disclosure provides methods and systems to assemble nucleic acid reads de novo, i.e., without the aid of a reference (e.g., a reference genome sequence). De novo assembly is often used in studying non-model organisms as their reference genome sequence often does not exist. De novo assembly is also used in transcriptome sequence data. A number of programs for de novo assembly have been developed, including SOAPdenovo-Trans, Velvet/Oases, Trans-ABySS and Trinity. Two basic algorithms have been generally used for de novo assemblers: overlap graphs and de Bruijn graphs. While the overlap graphs are used mostly for Sanger sequenced reads, as it is more computationally intensive than de Bruijn graphs and most effective in assembling fewer reads with a high degree of overlap. De Bruijn graphs align k-mers (usually 25-50 bp) based on k-1 sequence conservation to create contigs (contiguous, overlapping sequence reads). The use of k-mers, which are shorter than the read lengths, allows de Bruijn graphs methods to reduce the computational intensity and suitable for next-generation sequencing data.

In certain embodiments, a computation pipeline for de novo assembly comprises at least one invariable module, e.g., read cleaning and filtering module, and at least one variable module, e.g., contigging module. In passing the assembly pipeline, multiple values are set to variable parameters of the variable modules, e.g., k-mers for contigging module, while single values are set to invariable parameters of the invariable module. Thus, common computations can be saved between different parameter settings.

The following examples are presented to illustrate the present invention. They are not intended to limiting in any manner.

EXAMPLE 1

The following is an example of a computation pipeline with single-pass-multiple-settings for analyzing nucleic acid sequence reads.

The pipeline consists of the following modules connected in series: mapping module, duplicate marking module, local realignment module, base quality recalibration module and variant call module.

A SuperServer 6016T-NTF with Intel Dual Xeon E5620 2.4 Hz CPU, 48 GB DDR3 1333 MHz Ecc Memory, and 2 TB SATA Seagate ST32000644NS HDD is used to implement the pipeline.

The nucleic acid sequence reads analyzed is DNA exome sequencing data of a human genome.

The nucleic acid reads in FastQ format (generated by Illumina system) are fed to the mapping module, which mapped the reads to reference genome (human glk v37) using BWA algorithm. The mapping files in SAM format are sorted and converted to BAM format by SAMTools. The sorted BAM file is fed to the duplicate marking module, which used Picard to remove PCR duplicates. The BAM file with duplicates removed is fed to the local realignment module using GATK algorithm and dbSNP in Variant Call Format (vcf) as a reference. The realigned BAM file is fed to the base quality recalibration module, which used GATK algorithm.

The parameters for the above modules are set, for example as follows: 100 for the maximum offset between two duplicate clusters in order to consider them duplicates, 5.0 for LOD (Log of Odds) threshold in the local realignment model.

The recalibrated BAM file is then fed the variant call module using GATK algorithm. The module is passed 9 times to explore a 3×3 matrix: SNP (0.002, 0.001, 0.0005)× Indel (0.0002, 0.0001, 0.00005).

Results: it takes about 2300 min to run the single-pass-multiple-settings pipelined described above (for each module, the mapping module took about 40 min, the duplicate marking took about 40 min, the local realignment module took about 40 min, the base quality recalibration module took about 180 min and the variant call module took about 2000 min for running 9 times). In contrast, it takes about 4800 min to explore the matrix by running a comparable single-setting pipeline for 9 times. By using the recalibrated BAM file in the matrix of the variant call module, the total computation used in the above pipeline is only a small fraction of the computation otherwise required by passing a full-pipeline 9 times in order to explore the matrix.

While the invention has been particularly shown and described with reference to specific embodiments (some of which are preferred embodiments), it should be understood by those having skill in the art that various changes in form and detail may be made therein without departing from the spirit and scope of the present invention as disclosed herein.

What is claimed is:

1. A computer-implemented method for analyzing variants from at least a thousand nucleic acid sequence reads using a computation pipeline, wherein the at least a thousand nucleic acid sequence reads is obtained from high-throughput sequencing, said computation pipeline comprising an invariable module and a variable module, said variable module depending on a variable parameter, said method comprising executing on a processor the steps of:
   receiving the at least a thousand nucleic acid sequence reads;
   setting a plurality of variable values for said variable parameter;
   passing the at least a thousand nucleic acid sequence reads through said invariable module to generate an intermediate output;
   passing said intermediate output through said variable module for multiple rounds, each round using one of said plurality of variable values; and
   generating a plurality of variant calls.

2. The computer-implemented method of claim 1, wherein said variable module is a variant call module.

3. The computer-implemented method of claim 2, wherein said variable parameter is a prior probability.

4. The computer-implemented method of claim 3, wherein the prior probability is a genome-wide SNP probability, an insertion and deletion (Indel) probability, a Phred-scaled gap extension sequencing error probability, or a Phred-scaled gap open sequencing error probability.

5. The computer-implemented method of claim 1, wherein said invariable module is a mapping module, a duplicate marking module, a local realignment module, a base quality recalibration module, or a combination thereof.

6. The computer-implemented method of claim 1, wherein said invariable module depends on an invariable parameter, and wherein the method comprises the step of setting an invariable value for the invariable parameter.

7. The computer-implemented method of claim 1, further comprising the step of:
   reviewing at least one of said variant calls;
   setting an adjusted value for the variable parameter;
   passing said intermediate output through said variable module using the adjusted value; and
   generating an updated variant call.

8. A non-transitory computer-readable medium with instructions for analyzing variants from at least a thousand nucleic acid sequence reads using a computation pipeline stored thereon, wherein the at least a thousand nucleic acid sequence reads is obtained from high-throughput sequencing, said computation pipeline comprising an invariable module and a variable module, wherein said variable module depends on a variable parameter, said instructions when executed by a processor, performing the steps comprising:
   receiving the plurality of said nucleic acid sequence reads;
   setting a plurality of variable values for said variable parameter;
   passing the plurality of said nucleic acid sequence reads through said invariable module to generate an intermediate output;
   passing the intermediate output through said variable module for multiple rounds, each round using one of said plurality of variable values; and
   generating a plurality of variant calls.

9. The non-transitory computer-readable medium of claim 8, wherein said variable module is a variant call module.

10. The non-transitory computer-readable medium of claim 9, wherein said variable parameter is a prior probability.

11. The non-transitory computer-readable medium of claim 10, wherein the prior probability is a genome-wide SNP probability, an insertion and deletion (Indel) probability, a Phred-scaled gap extension sequencing error probability, or a Phred-scaled gap open sequencing error probability.

12. The non-transitory computer-readable medium of claim 8, wherein said invariable module is a mapping module, a duplicate marking module, a local realignment module, a base quality recalibration module, or a combination thereof.

13. The non-transitory computer-readable medium of claim 8, wherein said invariable module depends on an invariable parameter, and wherein the instructions when executed by a processor, performs the step of setting an invariable value for the invariable parameter.

14. The non-transitory computer-readable medium of claim 8, wherein the instructions when executed by a processor, performs the further steps comprising:
reviewing at least one of said variant calls;
setting an adjusted value for said variable parameter;
passing said intermediate output through said variable module using the adjusted value; and
generating an updated variant call.

15. A computer-implemented method for analyzing variants from at least a thousand nucleic acid reads using a computation pipeline, said computation pipeline comprising an invariable module and a variable module, wherein said variable module depends on a variable parameter, said method comprising executing on a processor the steps of:
receiving at least a thousand nucleic acid sequence reads obtained from high-throughput sequencing;
setting a first variable value for the variable parameter;
passing at least a thousand said nucleic acid sequence reads through said invariable module to generate an intermediate output;
passing said intermediate output through said variable module for a first round using the first variable value;
generating a first variant call;
reviewing the first variant call;
setting a second variable value for said variable parameter;
passing said intermediate output through said variable module for a second round using the second variable value; and
generating a second variant call.

16. The computer-implemented method of claim 15, wherein said variable module is a variant call module.

17. The computer-implemented method of claim 16, wherein the variable parameter is a prior probability.

18. The computer-implemented method of claim 17, wherein the prior probability is a genome-wide SNP probability, an insertion and deletion (Indel) probability, a Phred-scaled gap extension sequencing error probability, or a Phred-scaled gap open sequencing error probability.

19. The computer-implemented method of claim 15, wherein said invariable module is a mapping module, a duplicate marking module, a local realignment module, a base quality recalibration module, or a combination thereof.

20. The computer-implemented method of claim 15, wherein said invariable module depends on an invariable parameter, and wherein the method comprises the step of setting an invariable value for the invariable parameter.

* * * * *